(12) United States Patent
Colson

(10) Patent No.: US 10,322,027 B2
(45) Date of Patent: Jun. 18, 2019

(54) DENTAL BITE PLATE

(71) Applicant: Dana Colson, Toronto (CA)

(72) Inventor: Dana Colson, Toronto (CA)

(*) Notice: Subject to any disclaimer, the term of this patent is extended or adjusted under 35 U.S.C. 154(b) by 439 days.

(21) Appl. No.: 15/170,726

(22) Filed: Jun. 1, 2016

(65) Prior Publication Data

US 2017/0348141 A1   Dec. 7, 2017

(51) Int. Cl.
*A61F 5/56*   (2006.01)

(52) U.S. Cl.
CPC ........ *A61F 5/566* (2013.01); *A61F 2005/563* (2013.01)

(58) Field of Classification Search
CPC ...... A61F 5/56; A61F 5/566; A61F 2005/563; A63B 71/085; A63B 2071/086; A63B 2071/088; A61C 5/90; A61C 7/08
See application file for complete search history.

(56) References Cited

U.S. PATENT DOCUMENTS

| | | | |
|---|---|---|---|
| 2007/0079835 A1* | 4/2007 | Croll | A63B 71/085 128/859 |
| 2008/0053463 A1* | 3/2008 | Enoch | A61F 5/566 128/861 |
| 2008/0099029 A1* | 5/2008 | Lamberg | A61F 5/566 128/848 |
| 2010/0147315 A1* | 6/2010 | Chodorow | A61F 5/566 128/861 |
| 2011/0139162 A1* | 6/2011 | Chodorow | A61F 5/566 128/861 |
| 2013/0098375 A1* | 4/2013 | Urbanek | A61C 19/06 128/861 |
| 2014/0109919 A1* | 4/2014 | Crout | A61F 5/56 128/861 |
| 2016/0081767 A1* | 3/2016 | Metcalf | A61C 7/10 433/6 |

* cited by examiner

*Primary Examiner* — Kari K Rodriquez
(74) *Attorney, Agent, or Firm* — David W. Barman

(57) ABSTRACT

A bite plate configured for use on upper teeth only that is configured to envelope central incisors, lateral incisors, and optionally one of a portion of upper cuspid pairs or entire upper cuspid pairs with lateral extensions that enhances whole body wellness.

4 Claims, 9 Drawing Sheets

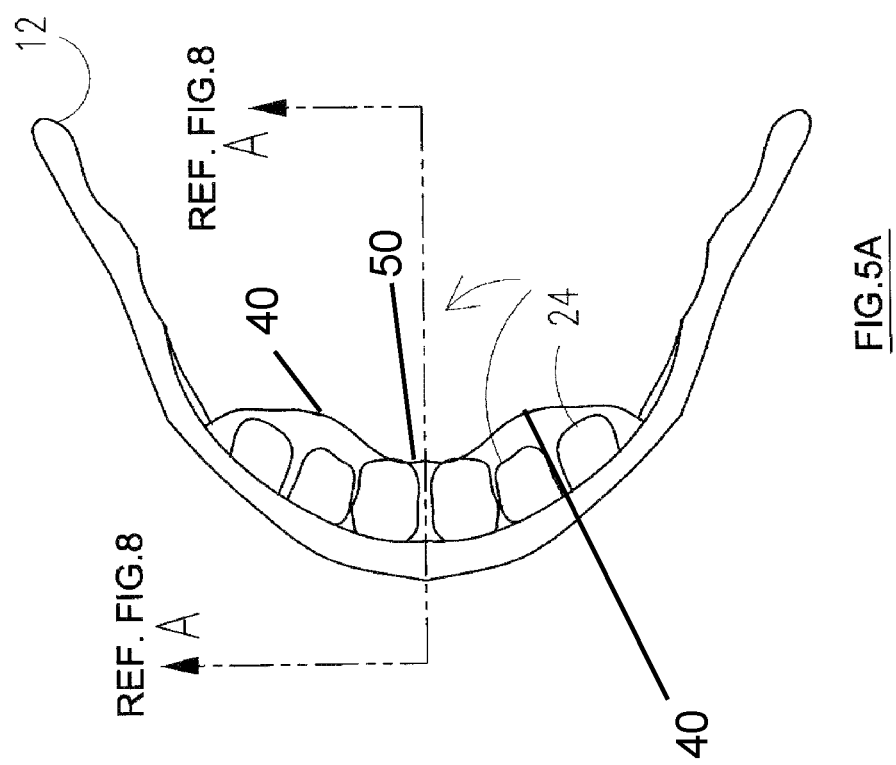

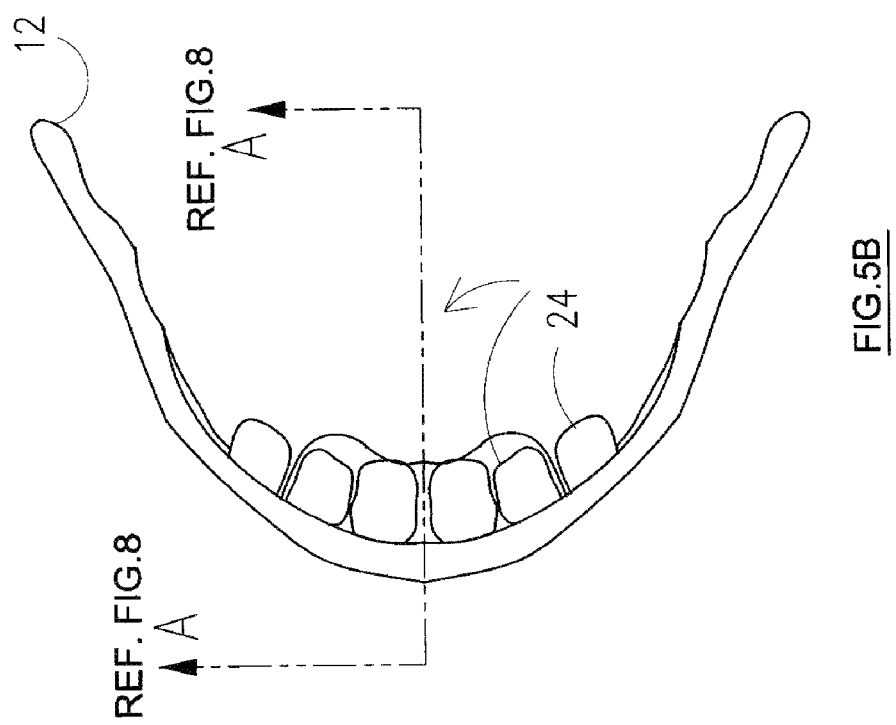

REF. FIG.7

DENTAL BITE PLATE

BACKGROUND OF THE INVENTION

Therapeutic bite plates are problematic in terms of comfort, patient satisfaction and patient compliance. People do not like to wear their bite plates as they gag with them, drool and have discomfort wearing so much rubber in their mouths. Most people are not aware that they grind and clench and are in denial. Often this habit is episodic and people do not know that they do it. The effects can be deleterious to their dentition, their facial muscles become thickened, the TMJ (temporo mandibular joint becomes compressed and altered), and often radiating pain occurs throughout the teeth, face, ear and neck. The TMJ may become a lifetime problem with deformation of the condyle (the top of the jaw bone) and the cartilage. Popping, clicki crepitus and locking of the jaw may occur with excessive stresses from this habit.

If the person has identified that they grind and clench and a bite plate is not worn it will not allow one to have their very best anti-aging part of their body, the smile, until 120+ years. When the bite plate is not worn the muscles continually contract at night and poor sleep occurs. Fractured teeth and collapse of the dentition happens if people do not wear their bite plate. Loss of teeth and possibly implants may be required with a heavy financial cost. Over time spacing will occur with drifting and shifting of the teeth. Less chewing function and fewer nutrients get released for healthy digestive uptake in our body.

The present invention addresses these and many more concerns.

SUMMARY OF THE INVENTION

The present invention prevents wearing of our teeth. Often, tooth wear occurs at night when we are in a subconscious state.

Excessive forces can occur while we sleep creating attrition, wear and fracture lines on our teeth. The mouth is a portal on how we nourish ourselves and our teeth act as the "utensils" to masticate our food to derive the nutrition from the food we eat so that our body can receive the nutrients and feed our cells to enable healthy lives. Tooth enamel once lost cannot be regenerated. The underlying dentin structure wears away faster than the inorganic enamel. Wear undermines the surrounding enamel and chips the enamel away. On the back teeth divots result in losing the cusp tips that are necessary for form and function not only for the individual tooth, but which can create excessive stress for the surrounding teeth that were not built for the functions that it then needs to fulfil. The incisors or front teeth lose their enamel incisal (biting) edge used for biting into food. The dentin is exposed here as well and wears faster than enamel. It is then undermined from further grinding and clenching and the surrounding walls of enamel that were undermined chip and break away even more (a continuous destructive cycle). Often a reverse smile line can occur, not easily fixed without spending thousands of dollars and having to sacrifice tooth structure to create a result that will require maintenance and possibly replacement over time. The gum tissue can also be altered or shrink away from the tooth causing "long in the tooth" or receding gums. This exposes cementum tooth structure at the gum line that can also erode and create hypersensitivity of the teeth to cold and sweets. Often stress lines occur and show as brown vertical lines leading to vertical fractures of the tooth. Occasionally the fracture is so severe the tooth requires a root canal and crown and occasionally it cannot be saved.

The configuration of the present invention is unique as it also allows the muscles of the mouth to relax, eliminates the activity of the temporal muscles and significantly lessens the constriction of the masseter muscle. The goal is to relax and limit muscle action to create a "calm" around us thus achieving a deeper sleep. The present invention separates the back teeth of the mouth that activate these muscles. The invention imparts a configuration whereby the lower front teeth skate/glide on a platform to prevent the molars and premolars from touching. When our back teeth do not touch (hence no grinding or clenching) we cannot activate our masticating muscles. These muscles, both the masseter and the temporalis are striated muscles. Striated muscles can develop trigger points in their fibers. These are little knots or round tissue masses. When palpated they elicit discomfort. The muscle can become enlarged and foreshortened. Discomfort radiates in all directions and can elicit many symptoms including the tension headache. This constitutes 70% of all headaches. Symptoms and severity varies from person to person. Imagine that we are activating our bicep muscle all night through exercise curls. The bicep muscle is also a striated muscle. How can we get a good night's sleep if we are continually contracting muscles? Thus by preventing the back teeth from touching the masseter (cheek muscle) and the temporalis muscle, movement is quieted. It has been documented that we can create up to 600 pounds of pressure per square inch at night grinding our teeth! Grinding is a circular jaw movement creating a wide platform of stress on the teeth while clenching is a tight vertical squeeze from the lower jaw onto the upper teeth. Both actions can create excessive and non-reversible damage.

INCLUDED BENEFITS OF THE PRESENT INVENTION

Benefits include, but are not limited to:
- helps prevent excessive forces of tooth grinding and clenching that cause fractures and worn teeth,
- stops movement of teeth as the heavy forces of grinding and clenching are eliminated
- decreases receding gums and "long in the tooth"
- reduces attrition (wear of the enamel, the hard external coating) of the biting edges of the teeth preventing shorter and sensitive teeth
- prevents tooth sensitivity as abfractions or notches are reduced at the CEJ (where the crown and root join) also known as toothbrush abrasions
- prevents excessive bony deposits in the jaw bone known as tori or exostosis of the bone
- prevents enlarged, often sore muscles and chubby cheeks,
- reduces tension headaches, radiating facial pain and twitching muscles,
- lessens or prevents clicking and grinding of the cartilage of the temporo-mandibular jaw joint (TMJ), mutilation of the cartilage, excessive wearing of the condyle (the head of the jaw bone) and displacement of the jaw bone in the TMJ.
- often enhances nasal airway flow
- decreases wrinkling of the upper lip
- can help decrease snoring
- ensures a "calm" when sleeping increasing the quality of sleep as the muscle contractions are significantly less The following section describes more detail about the above stated benefits. Additionally, the configuration of the present invention imparts the following advantages as it is a unique holistic and wellness based product that protects teeth, surrounding structures and enhances our well being.

The present invention does not need adjustments or fine tuning over time, unlike many other bite plates where you need equal intensity contact markings for balance, comfort and to reduce grinding and clenching. Other styles do not eliminate muscle activity thus the results are reduced significantly.

The present invention can prevent broken teeth, excessive mobility and movement of teeth and often receding gum tissues as pressures are relieved on the dentition.

The present invention can be easily modified to fit various concerns and intra-oral morphology by the consumer. A modification manual will be accessible for the individual online.

This is a minimally invasive bite plate ideal for people who have a tendency to gag or have a dislike of placing things in their mouths.

Wearing a bite plate of the present invention diminishes the foreshortening of muscles. The jaw bone does not infringe as much upon the cartilage space (located between the lower jaw bone and the upper jaw bone, respectively known as the mandible and the maxilla). When this temporo mandibular joint space is not constricted by muscle force, a major ingredient of the TMJ (temporal-mandibular joint) dysfunction is removed. The cartilage has more room to move with the lower jaw without bone interference, as the muscle contraction is significantly eliminated. Often "clicking" or "creaking" noises can be diminished along with significant pain, both local and referred.

The invention prevents headaches. This is very important because if one grinds or clenches their teeth at night, the temporalis muscle contracts excessively and constricts the blood vessels, producing tension headaches. By preventing the temporalis muscle from contracting and not constricting the blood vessels, the blood flow is not impaired and hence tension headaches are eradicated! Tension headaches comprise 70% of all headaches and are directly related to grinding and clenching teeth. These headaches mostly occur upon waking up in the morning or mid-day. There is a direct correlation with nocturnal muscle activity.

The invention is also a lip plumper for 7 hours a night. It prevents anti-aging of the upper lip.

The present invention with its lateral extensions between the back teeth and cheek, increases the intake of volume of air and thus more oxygen is inhaled through the nasal airway into our body.

The present invention is configured such that it does not infringe on the tongue space or palate unlike most other night time appliances. This is a huge bonus as extra material on one's palate often forces the tongue to reposition itself and to rest on the floor of the mouth inside the lower teeth. This forced tongue position has a greater chance to obstruct the airway space while sleeping and encourages mouth breathing and snoring. Mouth breathing causes dry mouth, as the lips do not create a seal. Intake of oxygen is only 80%. Over time, gum tissue can become inflamed and tooth decay occurs more rapidly. Teeth are more prone to shift and crowd as the upper jaw constricts over time. Snoring can diminish one's quality of sleep along with their partner's, causing for both partners tiredness. Over time depression for the non-snoring partner can result due to sleep deprivation. This bite plate does not claim to eliminate snoring nor mouth breathing and is not recommended for people with sleep apnea. It is suitable and an aid for those that grind and clench at night if they are wearing a CPAP.

Not only are our teeth used for chewing but also holding our jaw in the proper vertical alignment for our body to maximize our structural well-being. Our jaw in the right position can help our balance. The present invention can be used as a mouth guard for sports. A common phrase is "clench your teeth and you will be stronger!" Over 90% of the time the opposite is true in our population. Wearing the present invention creates better body balance and thus enhances muscle performance. When the teeth are separated the lower jaw will position itself in its innate best position. At this point, the body's optimal physiological adaptive range is achieved. The strength of this position can be verified through muscle kinesiology. When wearing a mouth guard for protection in sports we maximize performance with a better jaw position at the same time as protecting the teeth with this invention. The mouth guard provides greater comfort for the athlete as the space for the tongue is not infringed upon.

In one embodiment the invention is configured as a customized sports mouth guard that will be thicker with the same configuration and including a laminate behind the front teeth to cushion the possibility of heavy external forces. It can be ornamented with different colors and hold various logos or "tattoos". It will be more comfortable as well for the athlete.

The present invention creates awareness for golfers, horseback riders and other solo sports to keep the muscles relaxed, by ensuring there is limited clenching of muscles that radiate into the body enhancing sports performance.

There is no generic bite plate for children in the marketplace who grind and clench. Again, the present invention can be used for a dual purpose, for sleeping and sports and the comfortable design will allow for better compliance and acceptance. The child will have a better quality of sleep with less wear on their dentition.

This invention will be also marketed as an oral sex aid for stimulation. A smooth surface is preferable to tooth contact. This will be supplied with a thin lower tooth shield on the bottom teeth so that the surface area of stimulation will be doubled as the lips will stimulate as well as the bite plates covering the teeth.

In one embodiment, the present invention is a bite plate comprising:
  a main body configured to envelop upper tooth pairs including central incisors, lateral incisors, and optionally one of a portion of upper cuspid pairs or entire upper cuspid pairs; said main body further configured with a dual curvature positioned with a trough centered between the central incisors and congruent crests on either side of said trough; and lateral extensions between back teeth and cheek of a user body whereby unenveloped teeth extend downward past a lower peripheral surface of said lateral extensions of said main body.

In one embodiment, the main body is constructed and arranged to contact lower teeth at a contact point on each of the lower central incisors.

The present invention also includes a method of creating a defined distance of an air passageway when wearing a bite plate, said method comprising the steps of:
  providing a bite plate according to the invention described herein;
  opening a user's mouth;
  positioning said bite plate on upper teeth including central incisors, lateral incisors, and optionally one of a portion of upper cuspid pairs or entire upper cuspid pairs;
  closing a user's mouth;

imparting an air passageway of defined distance upon said closing.

In one embodiment the invention also includes a method for preventing contact of upper and lower back teeth, said method comprising the steps of:

provided a bite plate according to the invention described herein;

opening a user's mouth;

positioning said bite plate on upper teeth including central incisors, lateral incisors, and optionally one of a portion of upper cuspid pairs or entire upper cuspid pairs;

closing a user's mouth;

whereby upper and lower teeth positioned along said lateral extensions between back teeth and cheek of a user body whereby unenveloped teeth extend downward past a lower peripheral surface of said lateral extensions of said main body and said closing imparts a jaw position that prevents contact between said upper and lower teeth.

BRIEF DESCRIPTION OF THE SEVERAL VIEWS OF THE DRAWINGS

FIG. 5A is a top view of the bite plate according to one embodiment of the present invention positions about the six upper teeth (four incisors and 2 cuspids).

FIG. 5B is a top view of the bite plate according to one embodiment of the present invention positioned about the four incisor upper teeth.

DETAILED DESCRIPTION OF THE PREFERRED EMBODIMENT

The bite plate of the present invention is uniquely configured in that it is only worn on the upper teeth and actually does not cover all the upper teeth.

Figure 1:
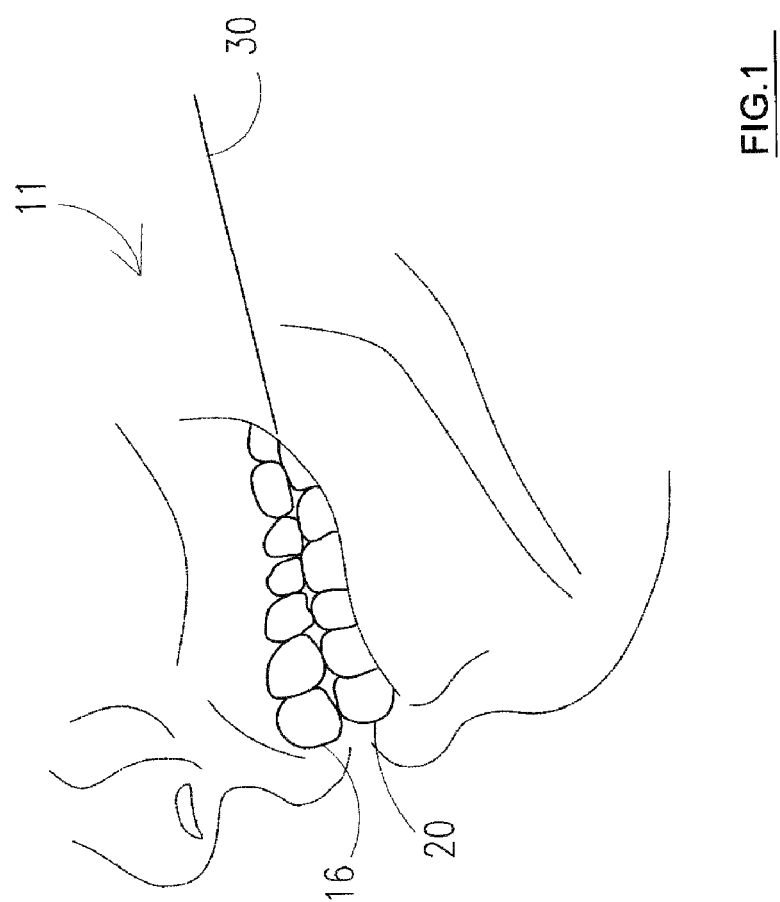
FIG. 1 is a lateral view demonstrating a closed jaw and the inter articulation of the upper and lower teeth.
Figure 2:
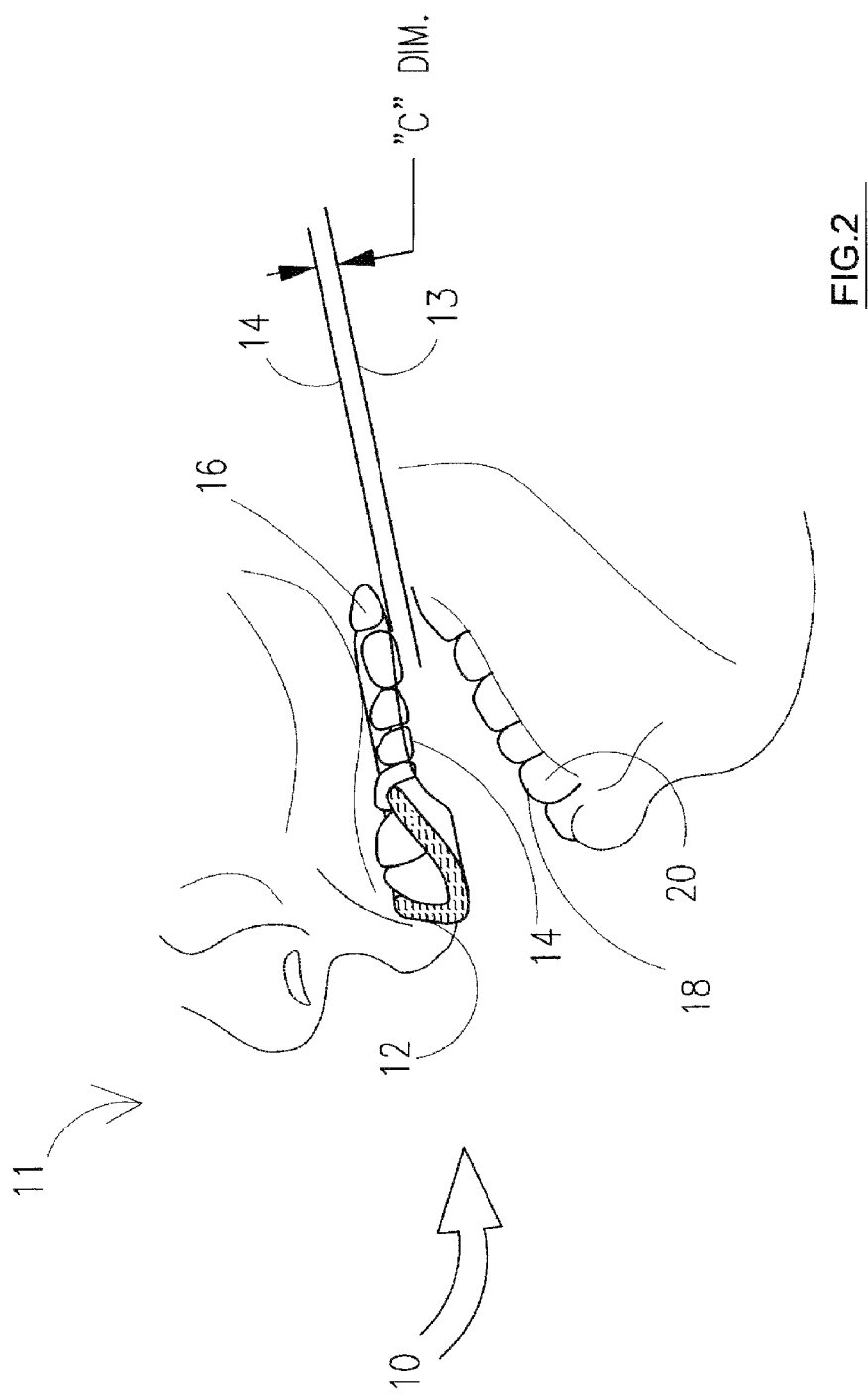
FIG. 2 is a lateral view with an open jaw and demonstrating placement of the bite plate according to one embodiment of the present invention.

Bite plate system 10 is worn by a user 11. System 10 includes a main body 12 having a main body lower surface 13 that contacts teeth 16 along the biting surface 14 of teeth 16. As demonstrated in FIG. 2, a person will open their jaw, position main body 12 on the front portion of upper teeth 16 subsequently closing their jaw as demonstrated in FIG. 3 whereby bite plate 12 contacts lower teeth 24 at contact point 22. Once the jaw is closed, Dimension C represents the distance created between the outer, lower surface 13 of bite plate 12 and the upper surface 18 of lower teeth 20.

Dimension C ideally is between about 2-5 mm. This measurement is dependent on the individual's bite and arrangement of their teeth.

Figure 3:
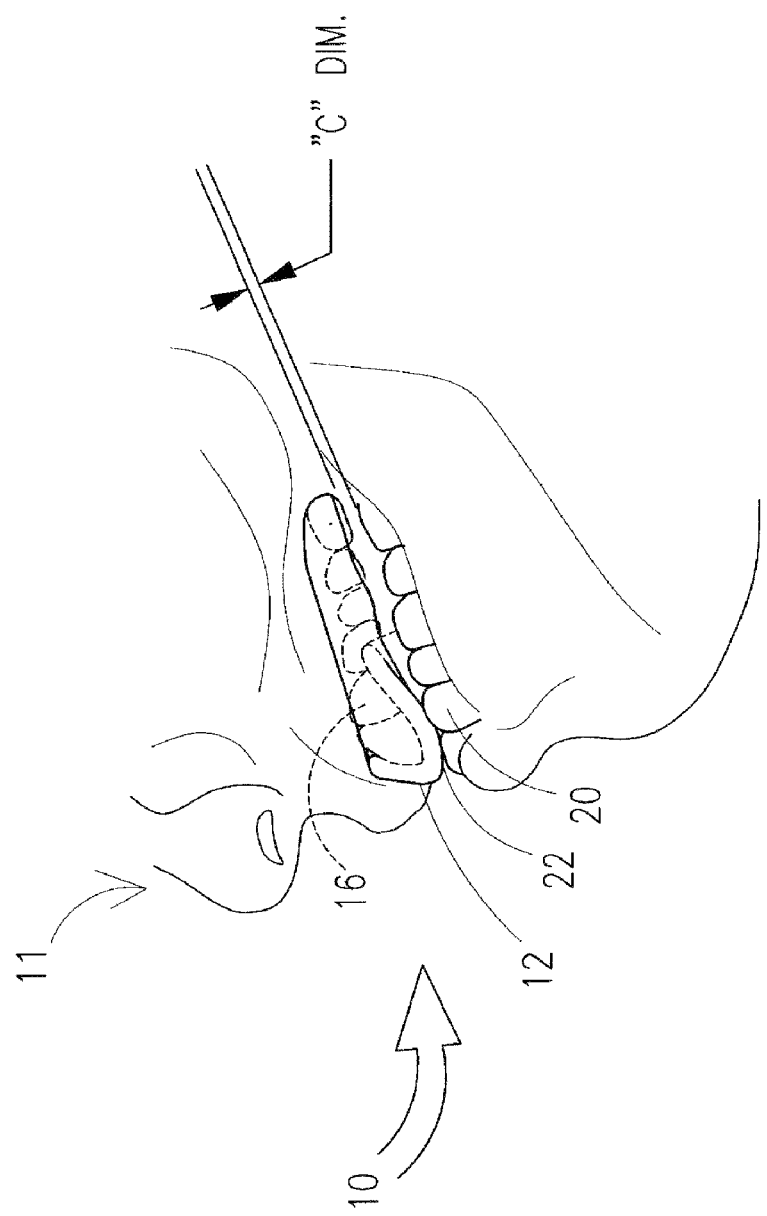
FIG. 3 is a lateral view demonstrating a closed jaw and placement of the bite plate according to one embodiment of the present invention.
Figure 4:
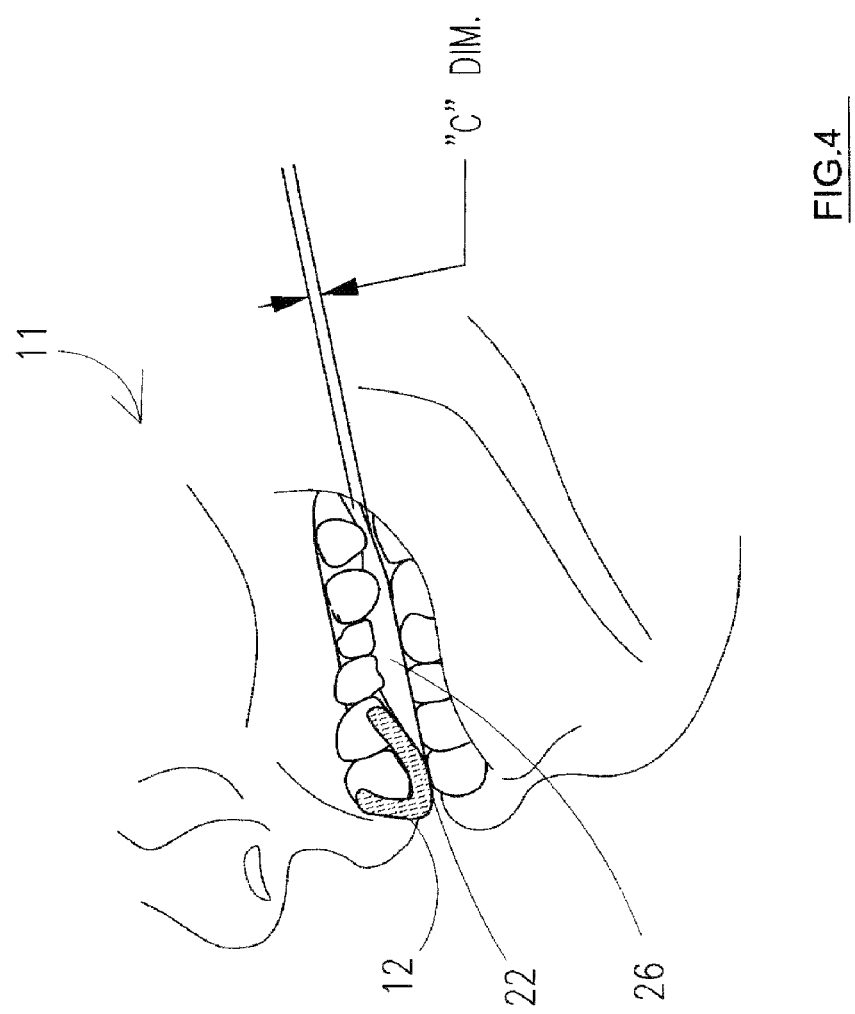
FIG. 4 is a lateral view demonstrating the bite plate contact point in a closed jaw and air passage according to one embodiment of the present invention.

As can be seen by will the configuration presented in FIG. 3 bite plate 12 prevent upper teeth 16 and lower teeth 20 from contacting one another. Further, as demonstrated in FIG. 4, in a passage 26 is of sufficient size to allow easy breathing.

Figure 5C:
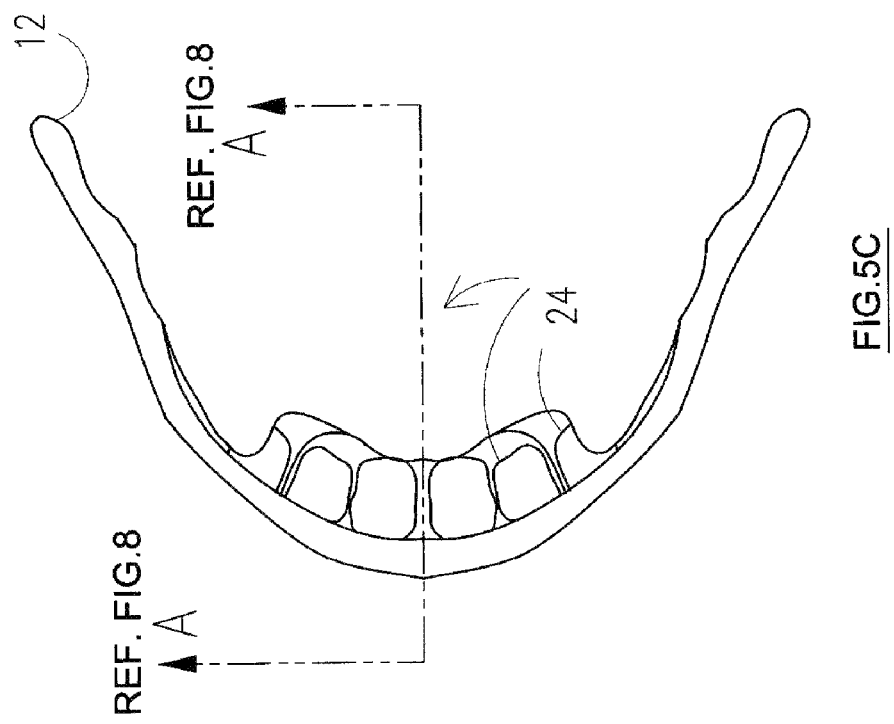
FIG. 5C is a top view of the bite plate according to one embodiment of the present invention positioned about the upper teeth. (A possible cut back for the user that eliminates masseter function to a greater percentage).

Although it is contemplated that the system 10 of the present invention used only on the upper teeth, it is further contemplated that not all of the upper teeth require to be enveloped with in the bite plate dental receiving cavity. In FIG. 5A, one embodiment is provided whereby only the first three pair of teeth being the central incisors, lateral incisors and cuspids, be inserted into main body 12. In FIG. 5B, one embodiment is provided whereby only the first two pair of teeth, being the central incisors and lateral incisors be inserted into main body 12. In FIG. 5C, one embodiment is provided whereby only the first two pair of teeth, being the central incisors and lateral incisors and only a portion of the cuspids are inserted into main body 12.

Figure 7:
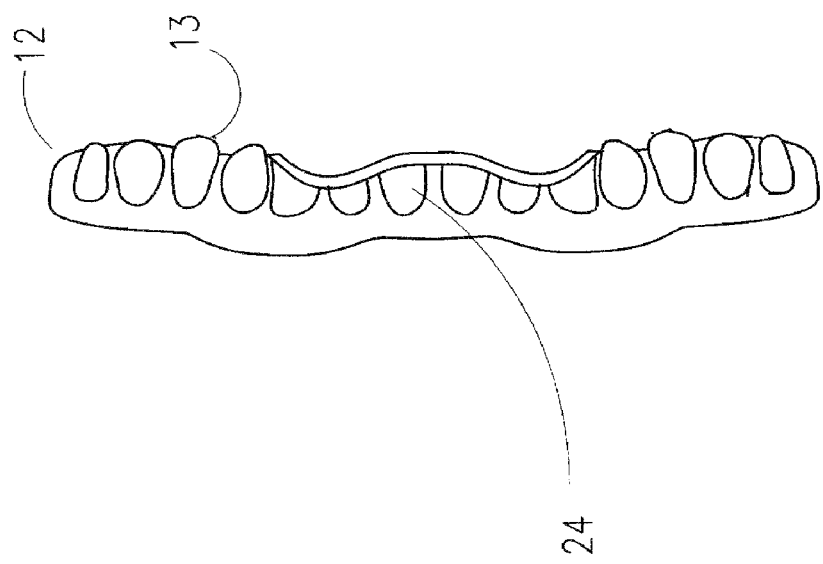
FIG. 7 is a lingual (inside) view of the bite plate in position according to one embodiment of the present invention.
Figure 6:
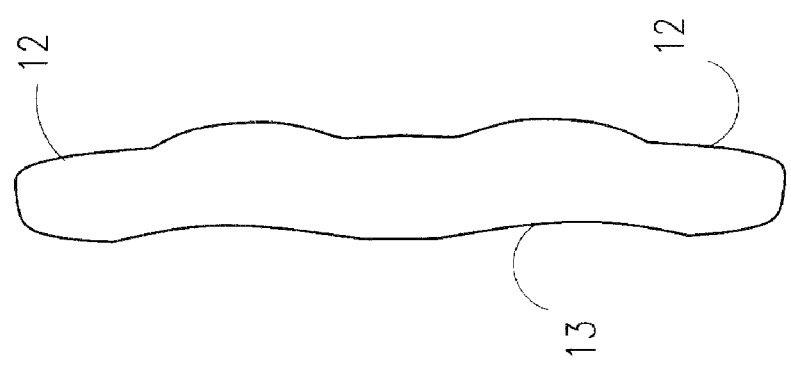
FIG. 6 is an anterior view of the bite plate with one embodiment of the present invention.
Figure 8:
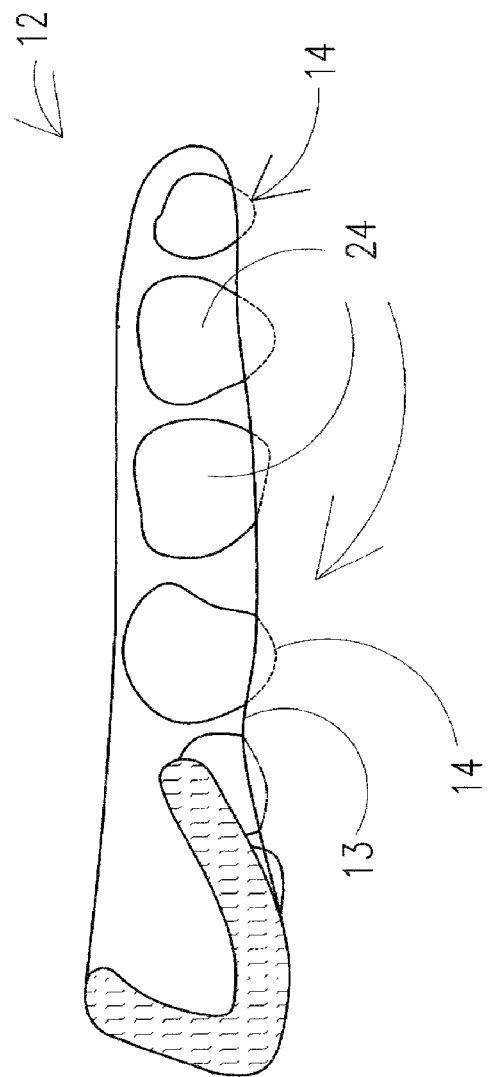
FIG. 8 is a lateral view of proposed bite plate on the maxillary (upper) dentition

As seen in FIGS. 5A 6 and 7, the center of main body 12 is configured with a dual curvature formed by two curved congruent crests 40 separated by a trough 50. This configuration imparts the correct positioning of the bite plate system 10 such that the objectives are achieved.

Additionally, bite plate main body 12 extends such that lower tooth surfaces 14 extend beyond the periphery of lower surface 13 of bite plate main body 12. Main body 12 has lateral extensions between back teeth and cheek of a user body whereby unenveloped teeth extend downward past a lower peripheral surface of said lateral extensions of said main body.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

I claim:

1. A bite plate comprising:
   a main body configured to envelop upper tooth pairs only including central incisors, lateral incisors, and optionally one of a portion of upper cuspid pairs or entire upper cuspid pairs;
   said main body further configured with a dual curvature positioned with a trough centered in use between each of the central incisors and congruent crests on either side of said trough; and
   lateral extensions having a free end adapted to be positioned on upper teeth of a user, whereby said lateral extensions extend along each of a tooth set including optionally upper cuspid, upper first bicuspid, upper second bicuspid, upper first molar and upper second molar configured with said extensions positioned between only back teeth of said tooth set and cheek of a user body along facial surface of said tooth set between said tooth set and cheek of a user in a passive manner, whereby unenveloped upper teeth in said tooth set extend downward past a lower peripheral surface of said lateral extensions of said main body.

2. The bite plate of claim 1, wherein said main body is constructed and arranged to contact lower teeth at a contact point on each of the lower central incisors.

3. A method of creating a defined distance of an air passageway when wearing a bite plate, said method comprising the steps of:
  providing a bite plate according to claim 1;
  opening a user's mouth;
  positioning said bite plate on upper teeth including central incisors, lateral incisors, and optionally one of a portion of upper cuspid pairs or entire upper cuspid pairs;
  closing a user's mouth;
  imparting an air passageway of defined distance upon said closing.

4. A method for preventing contact of upper and lower back teeth, said method comprising the steps of:
  providing a bite plate according to claim 1;
  opening a user's mouth;
  positioning said bite plate on upper teeth including central incisors, lateral incisors, and optionally one of a portion of upper cuspid pairs or entire upper cuspid pairs;
  closing a user's mouth;
  whereby upper and lower teeth positioned along said lateral extensions between back teeth and cheek of a user body whereby unenveloped teeth extend downward past a lower peripheral surface of said lateral extensions of said main body and said closing imparts a jaw position that prevents contact between said upper and lower teeth.

* * * * *